US007439403B2

(12) United States Patent
Hölscher

(10) Patent No.: US 7,439,403 B2
(45) Date of Patent: Oct. 21, 2008

(54) ALDEHYDES SUBSTITUTED IN ALPHA POSITION BY ALKYL RESIDUES AS ODORIFEROUS AND AROMA SUBSTANCES

(75) Inventor: Bernd Hölscher, Halle (DE)

(73) Assignee: Symrise GmbH & Co. KG, Holzminden (DE)

( * ) Notice: Subject to any disclaimer, the term of this patent is extended or adjusted under 35 U.S.C. 154(b) by 0 days.

(21) Appl. No.: 11/765,510

(22) Filed: Jun. 20, 2007

(65) Prior Publication Data

US 2008/0015392 A1 Jan. 17, 2008

(30) Foreign Application Priority Data

Jul. 11, 2006 (DE) ...................... 10 2006 032 317

(51) Int. Cl.
*C07C 47/02* (2006.01)
*A61K 8/18* (2006.01)

(52) U.S. Cl. ........................................ 568/448; 512/27

(58) Field of Classification Search ................. 568/448; 512/27
See application file for complete search history.

(56) References Cited

U.S. PATENT DOCUMENTS

| | | | | |
|---|---|---|---|---|
| 4,304,689 | A | 12/1981 | Boden et al. | |
| 5,481,044 | A * | 1/1996 | Weber et al. | 568/451 |
| 2006/0003913 | A1 | 1/2006 | Boutique et al. | |

FOREIGN PATENT DOCUMENTS

| | | |
|---|---|---|
| DE | 2719735 | 11/1977 |
| DE | 3942954 | 6/1991 |
| DE | 4344064 | 6/1995 |

OTHER PUBLICATIONS

Savoia et al., Potassium-Graphite as a Metalation Reagent, Synthesis of Aldehydes and Ketons by Alkylation of Imines and Dihydro-1,3-oxazine, J. Org. Chem., vol. 43, No. 14, 1978, pp. 2907-2910.

Bott, Aldehyde und Folgeprodukte aus der Oxo-Synthese von doppelbindungsisomerisierten n-Olefinen, Journal Fette, Seifen, Anstrichmittel, Chemische Werke Huls AG, 1974, 76(10), 443-446.

CAS No. 93821-14-8 with excerpt from the Arctander.

* cited by examiner

*Primary Examiner*—Sikarl A Witherspoon
(74) *Attorney, Agent, or Firm*—Roylance, Abrams, Berdo & Goodman, L.L.P.

(57) ABSTRACT

The present invention primarily relates to the use of an aldehyde, substituted in alpha position by an alkyl residue, of the formula

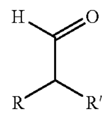

having (I) a total of 13 C atoms, wherein
 R means an unbranched alkyl residue having 6, 7, 8 or 9 C atoms and
 R' means an unbranched alkyl residue having 2, 3, 4 or 5 C atoms, or (II) a total of 15 C atoms, wherein
 R means an unbranched alkyl residue having 8, 9, 10 or 11 C atoms and
 R' means an unbranched alkyl residue having 2, 3, 4 or 5 C atoms, or a blend comprising or consisting of two, three or more such aldehydes of type (I) and/or (II),
as an odoriferous or aroma substance.

10 Claims, No Drawings

ALDEHYDES SUBSTITUTED IN ALPHA POSITION BY ALKYL RESIDUES AS ODORIFEROUS AND AROMA SUBSTANCES

FIELD OF THE INVENTION

The present invention relates to the use of specific aldehydes substituted in alpha position by an alkyl residue and having a total of 13 or a total of 15 C atoms as odoriferous or aroma substances. The invention additionally relates to perfumed or aromatized articles comprising such aldehydes and to corresponding methods for imparting, modifying and/or enhancing specific odor and/or flavor notes.

Methods for the production of suitable aldehydes and aldehyde blends are also described.

BACKGROUND OF THE INVENTION

Despite the multitude of odoriferous substances which are already available, there is still a general need in the perfume industry for new odoriferous substances. A need accordingly remains for odoriferous substances with aldehyde fragrance notes which (in odoriferous substance compositions) are capable of producing, in addition to aldehyde fragrance notes, further interesting odor notes and, with their novel or original fragrance properties, of extending options for the perfumer. In particular, there is interest in odoriferous substances with aldehyde fragrance notes which are capable of entering into a harmonious combination with woody-smelling odoriferous substances. The odorous aspects and notes should preferably combine in order, in so doing, to provide an overall complex odor impression.

For the purpose of creating modern compositions, there is a constant need for odoriferous substances with particular odorous properties which are suitable for acting as the basis for the composition of novel modern perfumes with complex odor properties. Odoriferous substances which are preferably sought should, in addition to an aldehyde fragrance note, comprises further notes and aspects which impart odorous character and complexity thereto.

SUMMARY OF THE INVENTION

The search for suitable odoriferous substances, which led to the present invention, was complicated by the following factors:

- The mechanisms of odor perception are not sufficiently known.
- The interrelationships between specific odor perception, on the one hand, and the chemical structure of the associated odoriferous substance, on the other hand, have not been adequately investigated.
- Even slight modifications to the structure of a known odoriferous substance often bring about major changes to organoleptic properties and impair compatibility with the human body.

The success of the search for suitable odoriferous substances is this highly dependent on the searcher's intuition.

The object underlying the present invention thus substantially involved identifying odoriferous substances with aldehyde fragrance notes which are combined with further interesting and original odorous properties, whereby the sought odoriferous substances permit novel and original odoriferous substance compositions with particular odorous notes and aspects. In particular, odoriferous substances with aldehyde fragrance notes were to be identified which are in particular suitable for combination with odoriferous substances which exhibit a woody fragrance note.

In addition, the odoriferous substances fulfilling this main object should furthermore preferably have additional positive secondary properties extending beyond their primary, namely odorous, properties, such as for example greater stability under specific conditions of use, higher yield, improved tenacity, elevated substantivity, a notable booster action or strong blooming, such that notable organoleptic effects or alternatively also better dermatological and toxicological properties may be achieved relative to comparable odoriferous substances.

DETAILED DESCRIPTION OF THE INVENTION

The stated primary object is achieved according to the invention by using an aldehyde, substituted in alpha position by an alkyl residue, of the formula

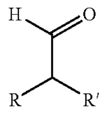

having (I) a total of 13 C atoms, wherein

R means an unbranched alkyl residue having 6, 7, 8 or 9 C atoms and

R' means an unbranched alkyl residue having 2, 3, 4 or 5 C atoms, or (II) a total of 15 C atoms, wherein R means an unbranched alkyl residue having 8, 9, 10 or 11 C atoms and R' means an unbranched alkyl residue having 2, 3, 4 or 5 C atoms, or a blend comprising or consisting of two, three or more such aldehydes of type (I) and/or (II), as an odoriferous or aroma substance.

The stated object is additionally achieved by using an aldehyde, substituted in alpha position by an alkyl residue, of the formula

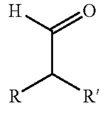

having (I) a total of 13 C atoms, wherein

R means an unbranched alkyl residue having 6, 7, 8 or 9 C atoms and

R' means an unbranched alkyl residue having 2, 3, 4 or 5 C atoms, or (II) a total of 15 C atoms, wherein R means an unbranched alkyl residue having 8, 9, 10, 11 or 12 C atoms and R' means an unbranched alkyl residue having 1, 2, 3, 4 or 5 C atoms, or a blend comprising or consisting of two, three or more such aldehydes of type (I) and/or (II), as an odoriferous or aroma substance with coniferous notes.

Further aspects emerge from the appended claims and the following description; these aspects here in particular relate to novel perfumed or aromatized articles and to corresponding methods.

The aldehydes to be used according to the invention comprise aldehydes having a total of 13 or a total of 15 C atoms. The aldehydes to be used are those of the formula

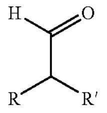

and have two unbranched alkyl residues R or R'. The following Table shows the aldehydes to be used according to the invention, the respective total number of C atoms and the respective number of C atoms in the residues R and R'.

TABLE 1

Overview of aldehydes to be used according to the invention

| Aldehydes to be used according to the invention | Total number of C atoms | Number of C atoms in R | Number of C atoms in R' |
|---|---|---|---|
| 2-Ethylundecanal | 13 | 9 | 2 |
| 2-Propyldecanal | 13 | 8 | 3 |
| 2-Butylnonanal | 13 | 7 | 4 |
| 2-Pentyloctanal | 13 | 6 | 5 |
| 2-Methyltetradecanal | 15 | 12 | 1 |
| 2-Ethyltridecanal | 15 | 11 | 2 |
| 2-Propyldodecanal | 15 | 10 | 3 |
| 2-Butylundecanal | 15 | 9 | 4 |
| 2-Pentyldecanal | 15 | 8 | 5 |

The odor properties of the aldehydes to be used according to the invention (see Table 1) are in each case described as follows: strongly aldehyde, clearer than other aldehydes, strongly coniferous, flowery, fatty sweet, ozone-like. In particular, the aldehydes of type (I) or (II) may be used to impart, modify and/or enhance a corresponding odor and/or flavor note.

The suitability of the aldehydes listed in Table 1, i.e. of the aldehydes to be used according to the invention, as odoriferous or aroma substances for use in the odor and aroma industry was hitherto unknown and is surprising.

The Journal of Organic Chemistry (1978), 43(14) 2907-2910 describes inter alia the production of 2-butylnonanal. However, no organoleptic description of this compound was provided.

German patent DE 43 44 064 C1 discloses a method for the production of aldehydes substituted in alpha position by an alkyl residue. One Example relates to the production of isomeric tridecanals from 1-dodecene. DE 43 44 064 C1 does not contain an organoleptic description of the aldehydes produced. Instead, it is explained that aldehydes having an 8 to 17 carbon atom molecule which are substituted by alkyl residues in alpha position to the carbonyl group are industrially significant intermediates.

German published patent application DE 39 42 954 A1 describes a method for the production of aldehydes by hydroformylation of olefinically unsaturated compounds. However, DE 39 42 954 A1 contains no organoleptic descriptions regarding the produced aldehydes.

The journal Fette, Seifen, Anstrichmittel (1974), 76(10), 443-446 inter alia provides indications regarding the synthesis of branched aldehydes by hydroformylation of isomerized alkenes. The publication does not provide an organoleptic description of the produced branched aldehydes.

The aldehydes tridecanal, methyl decyl acetaldehyde (2-methyldodecanal) and pentadecanal are already known from S. Arctander, Perfume and Flavor Materials, Vols. I and II, Montclair, N.J., 1969, private publication. Odor descriptions are also provided therein, which may be summarized as follows:

| | |
|---|---|
| tridecanal: | strongly waxy/fatty, freshly citrus, slightly flowery. |
| methyl decyl acetaldehyde: | dry waxy. |
| pentadecanal: | very slight, fresh/flowery. |

The stated publication (S. Arctander) classifies the aldehydes pentadecanal, methyl decyl acetaldehyde and tridecanal as overall not being of particular interest for perfumery. According to the published information, however, tridecanal appears to be of the greatest interest for perfumery, but this is an unbranched aldehyde and its odorous properties exhibit distinct differences from those of the aldehydes to be used according to the invention (see Table 1 above).

There is a reference under CAS registry number 93821-14-8 to specific hydroformylation products of C12-14 alkenes. A Celanese Chemicals publication on the internet contains a reference to a corresponding product. According to these references, the CAS number 93821-14-8 covers a blend of n/i-tridecanal and n/i-pentadecanal. There is, however, no odor description of the individual aldehydes contained in the blend. In particular, there is no odor description for i-pentadecanal, i.e. the compound 2-methyltetradecanal which is also to be used according to the invention. In particular, there is no indication that this compound has strong coniferous odor.

According to literature data, further already known aldehydes have a sweet, fatty/waxy, fresh/flowery odor with a weak balsamic undertone (lauraldehyde) or strong diffuse herbaceous aldehyde odor notes with a dry, ambergris-like undertone (methylundecanal).

The present invention is based on the recognition, which is surprising inter alia in the light of the referenced prior art, that the aldehydes to be used according to the invention (see Table 1 above) have mutually similar and furthermore better or other odor properties than the aldehydes tridecanal, methyl decyl acetaldehyde and pentadecanal which have already been described with regard to their odorous properties. The aldehydes to be used according to the invention are thus surprisingly particularly suitable as odoriferous and aroma substances.

In the light of the already above-described odor properties of the aldehydes to be used according to the invention, these are in particular used to impart, modify and/or enhance an odor and/or flavor note having the following aspects: aldehyde, coniferous, flowery, fatty sweet, ozone-like.

Within the bounds of use according to the invention, the aldehydes to be used according to the invention are conventionally used in organoleptically active quantities. The aldehydes to be used according to the invention should frequently be mixed with other odoriferous or aroma substances. These further odoriferous or aroma substances may comprise further aldehydes (including the above-stated aldehydes tridecanal, methyl decyl acetaldehyde and pentadecanal) or other odoriferous or aroma substances. The weight ratio of the total quantity of odoriferous substances to be used according to the invention (i.e. the odoriferous substances listed in Table 1) to the total quantity of further odoriferous or aroma substances is preferably in the range from 1:1000 to 1:0.5.

It is particularly preferred to use a blend comprising or consisting of two, three or more aldehydes of type (I) and/or of type (II). As is clear from the details provided further below regarding preferred production methods for aldehydes to be used according to the invention having a total of 13 or 15 C atoms, it is particularly simple to produce such aldehyde blends, and, when using the preferred production methods, it would entail additional effort to isolate individual produced aldehydes having a total of 13 or 15 C atoms and to use them in a form isolated from other aldehydes present in the produced aldehyde blend.

It is particularly suitable to combine aldehydes to be used according to the invention with woody odoriferous substances (including sandalwood, musk and ambergris) and flowery odoriferous substances. Woody odoriferous substances which are particularly suitable for being combined are: sandranol (2-ethyl-4-(2,2,3)-trimethylcyclopent-3-yl-but-2-en-1-ol), Ysamber K (1',1',5',5'-tetramethylhexahydro-spiro[1,3-dioxolan-2,8'(5'H)-2H-2,4a-methanonaphthalene]), Globanone (cyclohexadec-8-en-1-one), Timberol (1-(2,2,6-trimethylcyclohexyl)hexan-3-ol), iso E Super (2,3,8,8,-tetramethyl-1,2,3,4,5,6,8-octahydro-2-naphthalenyl-methyl ketone), Cashmeran (1,1,2,3,3-pentamethyl-TH-indan-4-one), isobornyl acetate (2-exo-bornanyl acetate), Ylanate (2-tert.-butylcyclohexyl acetate). Flowery odoriferous substances which are particularly suitable for being combined are: lilial (2-methyl-3-(4-tert-butylphenyl)propanal), hedione (methyl(3-oxo-2-pentylcyclopentyl)acetate), Mayol (4-isopropyl-cyclohexyl)methanol), linalool (3,7-dimethyl-1,6-octadien-3-ol), dihydromyrcenol (2,6-dimethyl-7-octen-2-ol), citronellol (3,7-dimethyl-6-octen-1-ol), Phenoxanol (3-methyl-5-phenyl-pentanol), 2-phenylethyl alcohol, hydroxycitronellal (3,7-dimethyl-7-hydroxyoctan-1-al), alpha-ionone (4-(2,6,6-trimethyl-cyclohex-2-enyl)-but-3-en-2-one).

Combining the aldehydes to be used according to the invention with the above-stated woody odoriferous substances gives rise to lighter and cleaner odor impressions. The blends have a more natural and fresher action.

The effect on combination with flowery odoriferous substances tends towards freshness and radiance. Flowery aspects are furthermore enhanced. The blends have a more intense and harmonious fragrance.

A combination with green/fruity odoriferous substances is furthermore frequently particularly preferred. Suitable green/fruity odoriferous substances are for example: Vertral (octahydro-1H-4,7-methanoindene 5-carbaldehyde), cis-3-hexen-1-ol, beta-damascone, (1-(2,6,6-trimethyl-cyclohex-2-enyl)-buten-1-one), Vertocitral (2,4-dimethylcyclohex-3-ene 1-carbaldehyde), cyclogalbanate (allyl (cyclohexyloxy) acetate), hexyl acetate.

A combination with the above-stated odoriferous substances gives rise to a rounder and softer odor. In addition, an impression of floweriness and a natural radiance is imparted by the addition of the aldehydes according to the invention.

A combination with spicy/balsamic odoriferous substances is furthermore frequently preferred. Suitable spicy/balsamic odoriferous substances are in particular: eugenol (2-methoxy-4-allylphenol), coumarin (2H-1-benzopyran-2-one), anisaldehyde (4-methoxybenzaldehyde), amylcinnamaldehyde (2-pentyl-3-phenyl-2-propenal), isoamyl salicylate (salicylic acid 3-methylbutyl ester) and cinnamyl alcohol (3-phenyl-2-propen-1-ol).

When aldehydes according to the invention are combined with the stated odoriferous substances, aspects of freshness and naturalness are observed. The blends have a more harmonious and radiant action.

The compounds to be used according to the invention according to Table 1 in each case have a chiral centre; they may have an R or S configuration or may be used as any desired mixture of the enantiomers, in particular as a racemate.

It is particularly surprising that the compounds to be used according to the invention according to Table 1 (aldehydes of types (I) and (II)) exhibit a pronounced aldehyde odor with in each case additional, in some case highly complex and multifaceted aspects, as the presence of these further additional aspects differentiates the compounds to be used according to the invention very distinctly from structurally comparable and known substances having aldehyde odor notes. See in particular the above statements regarding tridecanal, methyl decyl acetaldehyde and pentadecanal. Beyond their primary aldehyde fragrance note, the aldehydes or aldehyde blends to be used according to the invention in particular exhibit an unexpectedly strong coniferous and sweet odor with a surprising range of complex odor nuances. In particular, the blends of aldehydes to be used according to the invention and in particular blends of aldehydes of the formulae (I) and (II), i.e. of aldehydes to be used according to the invention with 13 and 15 C atoms, impart a very complex and highly diverse odor and flavor impression, which may otherwise only be achieved by complex blends of two or more components (such as for example by essential oils or herb or spice blends).

A preferred use of blends of aldehydes to be used according to the invention, is one in which the blends comprise one, two or more aldehydes of type (I) and one, two or more aldehydes of type (II) and wherein the weight ratio of the total quantity of aldehydes of type (I) to the total quantity of aldehydes of type (II) is in the range from 100:1 to 1:10, preferably in the range from 10:1 to 1:2 and particularly preferably in the range from 8:1 to 1:1. A blend ratio in the range from 5:1 to 2:1 is very particularly preferred.

If the aldehydes to be used according to the invention are to be combined with pentadecanal, methyl decyl acetaldehyde and/or tridecanal, the weight ratio of the total quantity of aldehydes of types (I) and (II) to the total quantity of pentadecanal, methyl decyl acetaldehyde and tridecanal is preferably in the range from 1:1000 to 1:0.1.

In blends with other odoriferous substances, the compounds of the formulae (I) and (II) to be used according to the invention are capable, even at low rates of addition, of enhancing the intensity of a odoriferous substance blend and of rounding and harmonizing the overall picture of the odoriferous substance blend and imparting greater radiance and naturalness to the blend.

Within the bounds of the use according to the invention of the above-stated aldehydes of types (I) and (II) as an odoriferous or aroma substance (in particular with a coniferous note), the present invention also relates to use for providing (a) hair, (b) skin or (c) textile fibers with an in particular aldehyde and simultaneously coniferous fragrance (see above with regard to further odor or flavor notes). The present invention also relates to corresponding methods and to blends (preferably containing surfactant). According to a related aspect, the present invention also relates to the use of the above-stated aldehydes of type (I) or (II) or of a blend comprising or consisting of two, three or more such aldehydes of type (I) and/or (II) as an agent for increasing the substantivity and/or retention of an odoriferous substance blend and/or as fixative and/or as an agent for increasing the odor of other odoriferous substances perceived from an aqueous solution containing surfactant.

The preferred use for modifying and/or enhancing an odor and/or flavor note is also associated with the recognition that the aldehydes of type (I) and/or (II) or of the corresponding blends to be used according to the invention may have an excellent action as a "booster" (enhancer).

Beyond their primary, namely odorous, properties, the aldehydes of type (I) or (II) or the corresponding blends to be used according to the invention have additional positive secondary properties, such as for example elevated stability under specific conditions of use, elevated yield, good tenacity, elevated substantivity.

Aldehydes of type (I) and/or (II) or corresponding blends may in particular be used to impart radiance, roundness and/or harmony to an odoriferous or aroma substance composition and/or to enhance existing odor and/or flavor notes.

The present invention also relates to perfumed or aromatized articles comprising (a) an aldehyde, substituted in alpha position by an alkyl residue, of the formula

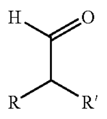

having (I) a total of 13 C atoms, wherein
  - R means an unbranched alkyl residue having 6, 7, 8 or 9 C atoms and
  - R' means an unbranched alkyl residue having 2, 3, 4 or 5 C atoms, or (II) a total of 15 C atoms, wherein
  - R means an unbranched alkyl residue having 8, 9, 10, 11 or 12 C atoms and
  - R' means an unbranched alkyl residue having 1, 2, 3, 4 or 5 C atoms, or a blend comprising or consisting of two, three or more such aldehydes of type (I) and/or (II), preferably in a quantity which is sufficient to impart, modify and/or enhance an odor or flavor note of the aldehyde, coniferous, flowery, fatty sweet and/or ozone-like type and (b) one, two, three or more further odoriferous or aroma substances, which in each case do not comprise an aldehyde with 13 or 15 C atoms, wherein the further odoriferous or aroma substance(s) preferably impart a woody and/or flowery odor and/or flavor.

Reference is made to the explanations provided further above with regard to the combination with particularly preferred odoriferous or aroma substances having a woody and/or flowery odor note.

The preferred developments of the invention described above with regard to the uses according to the invention, in particular the details regarding preferred ratios by weight, also apply mutatis mutandi to perfumed, aromatized articles according to the invention.

In addition to components (a) and (b), a perfumed or aromatized article according to the invention also comprises c) one, two or all the aldehydes from the group consisting of pentadecanal, methyl decyl acetaldehyde(2-methyldodecanal) and tridecanal.

The combination of component (a) with component (c) is in particular preferred because, with suitable control of the method, it is possible to produce aldehydes of components (a) and (c) in a common reaction batch. Depending on the specific design of the method, it is here possible to vary the proportions of said aldehydes. See further below with regard to production methods which give rise to blends of components (a) and (c).

A perfumed or aromatized article according to the invention preferably comprises an odoriferous or aroma substance composition. Novel odoriferous or aroma substance compositions may be formed by combining component (a) with a component (b), i.e. with one, two, three or more further odoriferous or aroma substances (preferably having a woody and/or flowery odor or flavor). Particularly interesting and natural novel and original fragrance notes may be created in this manner. Odoriferous substances (as component (b)) which are advantageously suitable for combining may be found, for example, in S. Arctander, Perfume and Flavor Materials, Vols. (I) and (II), Montclair, N.J. 1969, private publication, or K. Bauer et al., Common Fragrance and Flavor Materials, 4th edition, Wiley-VCH, Weinheim 2001. The following may be mentioned in detail:

extracts of natural raw materials such as essential oils, concretes, absolutes, resins, resinoids, balsams, tinctures such as for example:

ambergris tincture; amyris oil; angelica seed oil; angelica root oil; anise oil; valerian oil; basil oil; tree moss absolute; bay oil; artemisia oil; benzoin resin; bergamot oil; beeswax absolute; birch tar oil; bitter almond oil; savory oil; buchu leaf oil; cabreuva oil; cade oil; calmus oil; camphor oil; cananga oil; cardamom oil; cascarilla oil; cassia oil; cassie absolute; castoreum absolute; cedar leaf oil; cedarwood oil; cistus oil; citronella oil; lemon oil; copaiba balsam; copaiba balsam oil; coriander oil; costus root oil; cumin oil; cypress oil; davana oil; dill weed oil; dill seed oil; eau de brouts absolute; oak moss absolute; elemi oil; tarragon oil; eucalyptus citriodora oil; eucalyptus oil; fennel oil; pine-needle oil; galbanum oil; galbanum resin; geranium oil; grapefruit oil; guiacwood oil; gurjun balsam; gurjun balsam; helichrysum absolute; helichrysum oil; ginger oil; iris root absolute; iris root oil; jasmine absolute; calmus oil; camomile oil, blue; camomile oil, Roman; carrot seed oil; cascarilla oil; pine-needle oil; spearmint oil; caraway oil; labdanum oil; labdanum absolute; labdanum resin; lavandin absolute; lavandin oil; lavender absolute; lavender oil; lemongrass oil; lovage oil; lime oil, distilled; lime oil, pressed; linaloe oil; Litsea cubeba oil; bay leaf oil; mace oil; marjoram oil; mandarin oil; massoia bark oil; mimosa absolute; ambrette oil; musk tincture; muscatel sage oil; nutmeg oil; myrrh absolute; myrrh oil; myrtle oil; clove leaf oil; clove bud oil; neroli oil; olibanum absolute; olibanum oil; opopanax oil; orange blossom absolute; orange oil; origanum oil; palmarosa oil; patchouli oil; perilla oil;

Peru balsam oil; parsley leaf oil; parsley seed oil; petitgrain oil; peppermint oil; pepper oil; pimento oil; pine oil; pennyroyal oil; rose absolute; rosewood oil; rose oil; rosemary oil; sage oil, Dalmatian; sage oil, Spanish; sandalwood oil; celery seed oil; spike lavender oil; star anise oil; styrax oil; tagetes oil; fir needle oil; tea tree oil; terpentine oil; thyme oil; Tolu balsam; tonka absolute; tuberose absolute; vanilla extract; violet leaf absolute; verbena oil; vetiver oil; juniper berry oil; cognac oil; wormwood oil; wintergreen oil; ylang ylang oil; hyssop oil; civet absolute; cinnamon leaf oil; cinnamon oil and Fractions thereof, or constituents isolated therefrom;

individual odoriferous substances from the group of hydrocarbons, such as for example: 3-carene; α-pinene; β-pinene; α-terpinene; γ-terpinene; p-cymol; bisabolene; camphene; caryophyllene; cedrene; farnesene; limonene; longifolene; myrcene; ocimene; valencene; (E,Z)-1,3,5-undecatriene; styrene; diphenylmethane;

aliphatic alcohols such as for example hexanol; octanol; 3-octanol; 2,6-dimethylheptanol; 2-methyl-2-heptanol; 2-methyl-2-octanol; (E)-2-hexenol; 1-octen-3-ol; mixture of 3,4,5,6,6-pentamethyl-3/4-hepten-2-ol and 3,5,6,6-tetramethyl-4-methyleneheptan-2-ol; (E,Z)-2,6-nonadienol; 3,7-dimethyl-7-methoxyoctan-2-ol; 9-decenol; 10-undecenol; 4-methyl-3-decen-5-ol;

aliphatic aldehydes and the acetals thereof such as for example hexanal; heptanal; octanal; nonanal; decanal; undecanal; dodecanal; 2-methyloctanal; 2-methylnonanal; (E)-2-hexenal; (Z)-4-heptenal; 2,6-dimethyl-5-heptenal; 10-undecenal; (E)-4-decenal; 2-dodecenal; 2,6,10-trimethyl-9-undecenal; 2,6,10-trimethyl-5,9-undecadienal; heptanal diethylacetal; 1,1-dimethoxy-2,2,5-trimethyl-4-hexene; citronellyloxyacetaldehyde; 1-(1-methoxypropoxy)-(E/Z)-3-hexene;

aliphatic ketones and the oximes thereof such as for example 2-heptanone; 2-octanone; 3-octanone; 2-nonanone; 5-methyl-3-heptanone; 5-methyl-3-heptanone oxime; 2,4,4,7-tetramethyl-6-octen-3-one; 6-methyl-5-hepten-2-one;

aliphatic sulfur-containing compounds such as for example 3-methylthiohexanol; 3-methylthiohexyl acetate; 3-mercaptohexanol; 3-mercaptohexyl acetate; 3-mercaptohexyl butyrate; 3-acetylthiohexyl acetate; 1-menthen-8-thiol;

aliphatic nitriles such as for example 2-nonenoic acid nitrile; 2-undecenoic acid nitrile; 2-tridecenoic acid nitrile; 3,12-tridecadienoic acid nitrile; 3,7-dimethyl-2,6-octadienoic acid nitrile; 3,7-dimethyl-6-octenoic acid nitrile;

esters of aliphatic carboxylic acids such as for example (E)- and (Z)-3-hexenyl formate; ethyl acetoacetate; isoamyl acetate; 3,5,5-trimethylhexyl acetate; 3-methyl-2-butenyl acetate; (E)-2-hexenyl acetate; (E)- and (Z)-3-hexenyl acetate; octyl acetate; 3-octyl acetate; 1-octen-3-yl acetate; ethyl butyrate; butyl butyrate; isoamyl butyrate; hexyl butyrate; (E)- and (Z)-3-hexenyl isobutyrate; hexyl crotonate; ethyl isovalerate; ethyl-2-methyl pentanoate; ethyl hexanoate; allyl hexanoate; ethyl heptanoate; allyl heptanoate; ethyl octanoate; ethyl (E,Z)-2,4-decadienoate; methyl 2-octinate; methyl 2-noninate; allyl 2-isoamyloxyacetate; methyl 3,7-dimethyl-2,6-octadienoate; 4-methyl-2-pentyl crotonate;

acyclic terpene alcohols such as for example geraniol; nerol; lavandulol; nerolidol; farnesol; tetrahydrolinalool; tetrahydrogeraniol; 2,6-dimethyl-7-octen-2-ol; 2,6-dimethyloctan-2-ol; 2-methyl-6-methylene-7-octen-2-ol; 2,6-dimethyl-5,7-octadien-2-ol; 2,6-dimethyl-3,5-octadien-2-ol; 3,7-dimethyl-4,6-octadien-3-ol; 3,7-dimethyl-1,5,7-octatrien-3-ol, 2,6-dimethyl-2,5,7-octatrien-1-ol; and the formates, acetates, propionates, isobutyrates, butyrates, isovalerates, pentanoates, hexanoates, crotonates, tiglinates and 3-methyl-2-butenoates thereof;

acyclic terpene aldehydes and ketones such as for example citronellal; 7-methoxy-3,7-dimethyloctanal; 2,6,10-trimethyl-9-undecenal; geranyl acetone; and the dimethyl and diethyl acetals of geranial, neral, cyclic terpene alcohols such as for example menthol; isopulegol; alpha-terpineol; terpinen-4-ol; menthan-8-ol; menthan-1-ol; menthan-7-ol; borneol; isoborneol; linalool oxide; nopol; cedrol; ambrinol; vetiver oil; guaiol; and the formates, acetates, propionates, isobutyrates, butyrates, isovalerates, pentanoates, hexanoates, crotonates, tiglinates and 3-methyl-2-butenoates thereof;

cyclic terpene aldehydes and ketones such as for example menthone; isomenthone; 8-mercaptomenthan-3-one; carvone; camphor; fenchone; alpha-ionone; beta-ionone; alpha-n-methyl ionone; beta-n-methyl ionone; alpha-isomethyl ionone; beta-isomethyl ionone; alpha-irone; beta-damascenone; 1-(2,4,4-trimethyl-2-cyclohexen-1-yl)-2-buten-1-one; 1,3,4,6,7,8a-hexahydo-1,1,5,5-tetramethyl-2H-2,4a-methanonaphthalen-8(5H)-one; 2-methyl-4-(2,6,6-trimethyl-1-cyclohexen-1-yl)-2-butenal; nootkatone; dihydronootkatone; 4,6,8-megastigmatrien-3-one; alpha-sinensal; beta-sinensal; acetylated cedarwood oil (methyl cedryl ketone);

cyclic alcohols such as for example 4-tert.-butylcyclohexanol; 3,3,5-trimethylcyclohexanol; 3-isocamphylcyclohexanol; 2,6,9-trimethyl-Z2,Z5,E9-cyclododecatrien-1-ol; 2-isobutyl-4-methyltetrahydro-2H-pyran-4-ol;

cycloaliphatic alcohols such as for example alpha-3,3-trimethylcyclohexylmethanol; 1-(4-isopropylcyclohexyl)ethanol; 2-methyl-4-(2,2,3-trimethyl-3-cyclopent-1-yl)butanol; 2-methyl-4-(2,2,3-trimethyl-3-cyclopent-1-yl)-2-buten-1-ol; 3-methyl-5-(2,2,3-trimethyl-3-cyclopent-1-yl)-pentan-2-ol; 3-methyl-5-(2,2,3-trimethyl-3-cyclopent-1-yl)-4-penten-2-ol; 3,3-dimethyl-5-(2,2,3-trimethyl-3-cyclopent-1-yl)-4-penten-2-ol; 1-(2,2,6-trimethylcyclohexyl)pentan-3-ol; 1-(2,2,6-trimethylcyclohexyl)hexan-3-ol;

cyclic and cycloaliphatic ethers such as for example cineole; cedryl methyl ether; cyclododecyl methyl ether; 1,1-dimethoxycyclododecane; (ethoxymethoxy)cyclododecane; alpha-cedrene epoxide; 3a,6,6,9a-tetramethyldodecahydronaphtho[2,1-b]furan; 3a-ethyl-6,6,9a-trimethyldodecahydronaphtho[2,1-b]furan; 1,5,9-trimethyl-13-oxabicyclo[10.1.0]trideca-4,8-diene; rose oxide; 2-(2,4-dimethyl-3-cyclohexen-1-yl)-5-methyl-5-(1-methyl propyl)-1,3-dioxane;

cyclic and macrocyclic ketones such as for example 4-tert.-butylcyclohexanone; 2,2,5-trimethyl-5-pentylcyclopentanone; 2-heptylcyclopentanone; 2-pentylcyclopentanone; 2-hydroxy-3-methyl-2-cyclopenten-1-one; 3-methyl-cis-2-penten-1-yl-2-cyclopenten-1-one; 3-methyl-2-pentyl-2-cyclopenten-1-one; 3-methyl-4-cyclopentadecenone; 3-methyl-5-cyclopentadecenone; 3-methylcyclopentadecanone; 4-(1-ethoxyvinyl)-3,3,5,5-tetramethylcyclohexanone; 4-tert.-pentylcyclohexanone; 5-cyclohexadecen-1-one; 6,7-dihydro-1,1,2,3,3-pentamethyl-4(5H)-indanone; 8-cyclohexadecen-1-one; 9-cycloheptadecen-1-one; cyclopentadecanone; cyclohexadecanone;

cycloaliphatic aldehydes such as for example 2-methyl-4-(2,2,6-trimethyl-cyclohexen-1-yl)-2-butenal; 4-(4-hydroxy-4-methylpentyl)-3-cyclohexene carbaldehyde; 4-(4-methyl-3-penten-1-yl)-3-cyclohexene carbaldehyde;

cycloaliphatic ketones such as for example 1-(3,3-dimethylcyclohexyl)-4-penten-1-one; 2,2-dimethyl-1-(2,4-dimethyl-3-cyclohexen-1-yl)-1-propanone; 1-(5,5-dimethyl-1-cyclohexen-1-yl)-4-penten-1-one; 2,3,8,8-tetramethyl-1,2,3,4,5,6,7,8-octahydro-2-naphthalenyl methyl ketone; methyl- 2,6,10-trimethyl-2,5,9-cyclododecatrienyl ketone; tert.-butyl-(2,4-dimethyl-3-cyclohexen-1-yl)ketone;

esters of cyclic alcohols such as for example 2-tert.-butylcyclohexyl acetate; 4-tert.-butylcyclohexyl acetate; 2-tert.-pentylcyclohexyl acetate; 4-tert.-pentylcyclohexyl acetate; 3,3,5-trimethylcyclohexyl acetate; decahydro-2-naphthyl acetate; 2-cyclopentylcyclopentyl crotonate; 3-pentyltetrahydro-2H-pyran-4-yl acetate; decahydro-2,5,5,8a-tetramethyl-2-naphthyl acetate; 4,7-methano-3a,4,5,6,7,7a-hexahydro-5- or 6-indenyl acetate; 4,7-methano-3a,4,5,6,7,7a-hexahydro-5- or 6-indenyl propionate; 4,7-methano-3a,4,5,6,7,7a-hexahydro-5- or 6-indenyl isobutyrate; 4,7-methanooctahydro-5- or 6-indenyl acetate;

esters of cycloaliphatic alcohols such as for example 1-cyclohexylethyl crotonate;

esters of cycloaliphatic carboxylic acids such as for example allyl 3-cyclohexylpropionate; allyl cyclohexyloxyacetate; cis- and trans-methyl dihydrojasmonate; cis- and trans-methyl jasmonate; methyl 2-hexyl-3-oxocyclopentanecarboxylate; ethyl 2-ethyl-6,6-dimethyl-2-cyclohexenecarboxylate; ethyl 2,3,6,6-tetramethyl-2-cyclohexenecarboxylate; ethyl 2-methyl-1,3-dioxolane-2-acetate;

araliphatic alcohols such as for example benzyl alcohol; 1-phenylethyl alcohol; 3-phenylpropanol; 2-phenylpropanol; 2-phenoxyethanol; 2,2-dimethyl-3-phenylpropanol; 2,2-dimethyl-3-(3-methylphenyl)propanol; 1,1-dimethyl-2-phenylethyl alcohol; 1,1-dimethyl-3-phenylpropanol; 1-ethyl-1-methyl-3-phenylpropanol; 2-methyl-5-phenylpentanol; 3-methyl-5-phenylpentanol; 3-phenyl-2-propen-1-ol; 4-methoxybenzyl alcohol; 1-(4-isopropylphenyl)ethanol;

esters of araliphatic alcohols and aliphatic carboxylic acids such as for example benzyl acetate; benzyl propionate; benzyl isobutyrate; benzyl isovalerate; 2-phenylethyl acetate; 2-phenylethyl propionate; 2-phenylethyl isobutyrate; 2-phenylethyl isovalerate; 1-phenylethyl acetate; alpha-trichloromethylbenzyl acetate; alpha,alpha-dimethylphenylethyl acetate; alpha,alpha-dimethylphenylethyl butyrate; cinnamyl acetate; 2-phenoxyethyl isobutyrate; 4-methoxybenzyl acetate;

araliphatic ethers such as for example 2-phenyl ethyl methyl ether; 2-phenyl ethyl isoamyl ether; 2-phenyl ethyl-1-ethoxyethyl ether; phenylacetaldehyde dimethylacetal; phenylacetaldehyde diethylacetal; hydratropaldehyde dimethylacetal; phenylacetaldehyde glycerol acetal; 2,4,6-trimethyl-4-phenyl-1,3-dioxane; 4,4a,5,9b-tetrahydroindolyl[1,2-d]-m-dioxin; 4,4a,5,9b-tetrahydro-2,4-dimethylindeno[1,2-d]-m-dioxin;

aromatic and araliphatic aldehydes such as for example benzaldehyde; phenylacetaldehyde; 3-phenylpropanal; hydratropaldehyde; 4-methylbenzaldehyde; 4-methylphenylacetaldehyde; 3-(4-ethylphenyl)-2,2-dimethylpropanal; 2-methyl-3-(4-isopropylphenyl)propanal; 2-methyl-3-(4-isobutylphenyl)propanal; 3-(4-tert.-butylphenyl)propanal; cinnamaldehyde; alpha-butylcinnamaldehyde; alpha-hexylcinnamaldehyde; 3-methyl-5-phenylpentanal; 4-methoxybenzaldehyde; 4-hydroxy-3-methoxybenzaldehyde; 4-hydroxy-3-ethoxybenzaldehyde; 3,4-methylenedioxybenzaldehyde; 3,4-dimethoxybenzaldehyde; 2-methyl-3-(4-methoxyphenyl)propanal; 2-methyl-3-(4-methylenedioxyphenyl)propanal;

aromatic and araliphatic ketones such as for example acetophenone; 4-methylacetophenone; 4-methoxyacetophenone; 4-tert.-butyl-2,6-dimethylacetophenone; 4-phenyl-2-butanone; 4-(4-hydroxyphenyl)-2-butanone; 1-(2-naphthalenyl)ethanol; 2-benzofuranylethanone; (3-methyl-2-benzofuranyl)ethanol; benzophenone; 1,1,2,3,3,6-hexamethyl-5-indanyl methyl ketone; 6-tert.-butyl-1,1-dimethyl-4-indanyl methyl ketone; 1-[2,3-dihydro-1,1,2,6-tetramethyl-3-(1-methylethyl)-1H-5-indenyl]ethanone; 5',6',7',8'-tetrahydro-3',5',5',6',8',8'-hexamethyl-2-acetonaphthone;

aromatic and araliphatic carboxylic acids and the esters thereof such as for example benzoic acid; phenylacetic acid; methyl benzoate; ethyl benzoate; hexyl benzoate; benzyl benzoate; methylphenyl acetate; ethylphenyl acetate; geranylphenyl acetate; phenylethylphenyl acetate; methyl cinnamate; ethyl cinnamate; benzyl cinnamate; phenylethyl cinnamate; cinnamyl cinnamate; allyl phenoxy acetate; methyl salicylate; hexyl salicylate; cyclohexyl salicylate; cis-3-hexenyl salicylate; benzyl salicylate; phenylethyl salicylate; methyl 2,4-dihydroxy-3,6-dimethylbenzoate; ethyl-3-phenyl glycidate; ethyl-3-methyl-3-phenyl glycidate;

nitrogenous aromatic compounds such as for example 2,4,6-trinitro-1,3-dimethyl-5-tert.-butylbenzene; 3,5-dinitro-2,6-dimethyl-4-tert.-butyl acetophenone; cinnamonitrile; 3-methyl-5-phenyl-2-pentenoic acid nitrile; 3-methyl-5-phenylpentanoic acid nitrile; methyl anthranilate; methyl-N-methyl anthranilate; Schiff bases of methyl anthranilate with 7-hydroxy-3,7-dimethyloctanal, 2-methyl-3-(4-tert.-butylphenyl)propanal or 2,4-dimethyl-3-cyclohexene carbaldehyde; 6-isopropyl quinoline; 6-isobutyl quinoline; 6-sec.-butyl quinoline; 2-(3-phenylpropyl)pyridine; indole; skatole; 2-methoxy-3-isopropylpyrazine; 2-isobutyl-3-methoxypyrazine;

phenols, phenyl ethers and phenyl esters such as for example estragole; anethole; eugenyl methyl ether; isoeugenol; isoeugenyl methyl ether; thymol; carvacrol; diphenyl ether; beta-naphthyl methyl ether; beta-naphthyl ethyl ether; beta-naphthyl isobutyl ether; 1,4-dimethoxybenzene; eugenyl acetate; 2-methoxy-4-methylphenol; 2-ethoxy-5-(1-propenyl)phenol; p-cresyl phenyl acetate;

heterocyclic compounds such as for example 2,5-dimethyl-4-hydroxy-2H-furan-3-one; 2-ethyl-4-hydroxy-5-methyl-2H-furan-3-one; 3-hydroxy-2-methyl-4H-pyran-4-one; 2-ethyl-3-hydroxy-4H-pyran-4-one;

lactones such as for example 1,4-octanolide; 3-methyl-1,4-octanolide; 1,4-nonanolide; 1,4-decanolide; 8-decen-1,4-olide; 1,4-undecanolide; 1,4-dodecanolide; 1,5-decanolide; 1,5-dodecanolide; 4-methyl-1,4-decanolide; 1,15-pentadecanolide; 1,16-hexadecanolide; 9-hexadecen-1,16-olide; 10-oxa-1,16-hexadecanolide; 11-oxa-1,16-hexadecanolide; 12-oxa-1,16-hexadecanolide; ethylene 1,12-dodecanedioate; ethylene 1,13-tridecanedioate; 2,3-dihydrocoumarin; octahydrocoumarin.

An odoriferous or aroma substance composition according to the invention may, for example, be produced by preparing a component (a) or a blend of components (a) and (c) and mixing this component or blend with one or more further odoriferous or aroma substances (as component (b)). Component (a) is here regularly used in a quantity which, in the finished composition, is sufficient to impart, to modify and/or to enhance an odor or flavor note of the aldehyde, coniferous, flowery, fatty/sweet and/or ozone-like type.

An odoriferous or aroma substance composition according to the invention preferably comprises a total quantity the component (a) in the range from 0.00001 to 99.9 wt. %, preferably 0.001 to 70 wt. % and particularly preferably 0.01 to 50 wt. %, relative to the total quantity of odoriferous or aroma substance composition.

If the aldehydes or a corresponding blend to be used according to the invention are/is mainly used in order to impart more radiance, roundness and/or harmony to an odoriferous or aroma substance composition and/or to enhance specific notes, the total quantity of component (a) is preferably comparatively low and particularly preferably in the range from 0.01 to 5 wt. %, preferably in the range from 0.1 to 2 wt. %, relative to the total quantity of the odoriferous or aroma substance composition. If, within the preferred concentration ranges, a comparatively low concentration is selected, depending on the further components of the particular composition, in many cases the above-stated intrinsic odor or flavor notes are not yet imparted.

The aldehydes of type (I) or (II) or corresponding blends to be used according to the invention may be produced by means of per se known reactions and methods.

The aldehydes may, for example, be synthesized by alkylating imines and dihydro-1,3-oxazines in an analogous manner to the instructions in Journal of Organic Chemistry (1978), 43(14) 2907.

Alternatively, the aldehydes or aldehyde blends to be used according to the invention may be obtained by hydroformylation starting from olefins of the following formulae A or B.

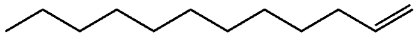

A

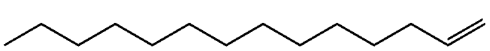

B

Hydroformylation (oxo synthesis) of a compound A and/or B is carried out with synthesis gas (a mixture of carbon monoxide and hydrogen) in the presence of transition metal catalysts (frequently from subgroup VII). This reaction may be carried out on the basis of hydroformylation reactions of dienes, such as for example of n-tetradec-1-ene. The reaction may here be carried out under homogeneous or heterogeneous conditions. Co or Rh catalysts are conventionally used for hydroformylation. The hydroformylation according to the invention of compound A and/or B is preferably carried out on the basis of DE 39 42 954 A1 and DE 43 44 064.

Reference is made to the explanations in said publications with regard to reaction parameters, in particular with regard to preferred catalysts, ligands, solvents or diluents, temperature, pressure, duration of reaction, homogeneous or heterogeneous reaction control, working up etc.

In a mariner similar to DE 39 42 954 A1, a blend may be formed from a compound A and/or B by means of hydroformylation in the presence of a rhodium catalyst such as Rh 2-ethylhexanoate, which blend, in addition to the aldehydes to be used according to the invention, also comprises pentadecanal, methyl decyl acetaldehyde and/or tridecanal.

Under conventional production (hydroformylation) conditions of aldehydes of type (I) and/or (I) to be used according to the invention by means of hydroformylation of the corresponding olefins of the above formulae A and/or B, migration (isomerization) of the olefinic double bond occurs in part, such that the organoleptically valuable aldehydes of type (I) or (II) to be used according to the invention also arise and not only the aldehydes pentadecanal, methyl decyl acetaldehyde and/or tridecanal which have already been described with regard to their odorous properties. It is particularly preferred according to the invention to use aldehydes of type (I) and/or (II) whose R' residue comprises at least two C atoms. A particularly elevated proportion of the organoleptically valuable aldehydes of type (I) or (II) may, for example, be obtained by a production method in which, in a first step, terminal olefins are isomerized to yield interior olefins and, in a second step, hydroformylation is carried out, for example in a similar manner to DE 43 44 064. Alternatively, the details regarding production methods as described in Fette, Seifen, Anstrichmittel (1974), 76(10), 443-446 may be followed.

If, as a result of the production method, individual aldehydes of type (I) or (II), i.e. the aldehydes listed in Table 1, are present in the reaction mixture, in particular in addition to further aldehydes to be used according to the invention and/or pentadecanal, methyl decyl acetaldehyde and/or tridecanal, they may preferably be isolated from the reaction mixture by means of conventional methods such as distillation or rectification. If required, accurate separation or extensive purification may proceed for example by means of fractionation in a rotating-strip column, by means of HPLC or preparative gas chromatography.

Odoriferous or aroma substance compositions according to the invention containing aldehydes of type (I) and/or (II) may be used for perfuming or aromatization in liquid form, undiluted or diluted with a solvent. Solvents suitable for this purpose are for example ethanol, isopropanol, diethylene glycol monoethyl ether, glycerol, propylene glycol, 1,2-butylene glycol, dipropylene glycol, diethyl phthalate, triethyl citrate, isopropyl myristate, triacetin etc.

Moreover, odoriferous or aroma substance compositions according to the invention containing aldehydes of type (I) and/or (II) may be adsorbed onto a carrier which ensures not only a fine distribution of the odoriferous or aroma substances in the product but also controlled release on use. Such carriers may be porous inorganic materials such as light sulfate, silica gels, zeolites, gypsums, clays, clay granules, aerated concrete etc. or organic materials such as woods, cellulose-based substances, sugars, dextrins (for example maltodextrin) or plastics such as PVC, polyvinyl acetates or polyurethanes. The combination of composition according to the invention and carrier is one example of an article according to the invention.

Odoriferous or aroma substance compositions according to the invention containing aldehydes of type (I) and/or (II) may also be present in microencapsulated form, spray-dried form, as inclusion complexes or as extrusion products (i.e. articles according to the invention) and be added in this form for example to a product to be perfumed or aromatized.

Optionally, the properties of the compositions modified in this way may be further optimized with regard to more targeted fragrance release by "coating" with suitable materials, for which purpose waxy plastics such as for example polyvinyl alcohol are preferably used. The resultant products are in turn articles according to the invention.

The odoriferous or aroma substance compositions according to the invention may be encapsulated to yield articles according to the invention, for example, by "coacervation" methods with the assistance of capsule materials for example made from polyurethane-type substances or soft gelatin. Spray-dried odoriferous or aroma substance compositions may be produced for example by spray drying an emulsion or dispersion containing the odoriferous or aroma substance composition, wherein modified starches, proteins, dextrin and vegetable gums may be used as carriers. Inclusion complexes may be produced for example by introducing dispersions of the odoriferous or aroma substance composition and cyclodextrins or urea derivatives into a suitable solvent, for example water. Extrusion products may be produced by melting the odoriferous or aroma substance compositions with a suitable waxy substance and extrusion with subsequent solidification, optionally in a suitable solvent, for example isopropanol.

Aldehydes of type (I) and/or (II) and odoriferous or aroma substance compositions containing compounds of type (I) and/or (II) may be used in concentrated form, in solutions or in an above-described modified form for the production of perfumed articles according to the invention, such as for example perfume extracts, eaux de parfum, eaux de toilette, shaving lotions, eaux de cologne, preshave products, splash colognes and perfumed tissue wipes and to perfume acidic, alkaline and neutral cleaning agents, such as for example floor cleaners, window cleaners, dishwashing detergents, bath and sanitary cleaners, scouring cream, solid and liquid toilet cleaners, pulverulent and foam carpet cleaners, textile fresheners, ironing aids, liquid detergents, pulverulent detergents, laundry pretreatment agents, such as bleaches, soaking agents and stain removers, laundry rinse conditioners, laundry soaps, laundry tablets, disinfectants, and surface disinfectants as well as air fresheners in liquid or gel form or applied to a solid carrier, aerosol sprays, waxes and polishes such as furniture polishes, floor waxes, shoe polishes as well as body care products such as for example solid and liquid soaps, shower gels, shampoos, shaving soaps, shaving foams, bath oils, cosmetic emulsions of the oil-in-water, water-in-oil and water-in-oil-in-water type, such as for example skin creams and lotions, face creams and lotions, sunscreen creams and lotions, after-sun creams and lotions, hand creams and lotions, foot creams and lotions, depilatory creams and lotions, after-shave creams and lotions, tanning creams and lotions, hair care products such as for example hair sprays, hair gels, strengthening hair lotions, hair rinses, permanent and semi-permanent hair dyes, hair styling agents such as cold waving and hair straightening agents, hair tonics, hair creams and lotions, deodorants and antiperspirants such as for example underarm sprays, roll-ons, deodorant sticks, deodorant creams, decorative cosmetic products such as for example eyeshadows, nail varnishes, make-up products, lipsticks, mascara and candles, lamp oils, incense sticks, insecticides, repellants and fuels.

The aldehydes of type (I) and/or (II) or the corresponding blends may be incorporated into articles which are aromatized or are to be aromatized, in particular into preparations consumed for nutrition or for pleasure or used for oral care.

The preparations consumed for nutrition or for pleasure are for example bakery products (for example bread, dry biscuits, cakes, other pastry products), confectionery (for example chocolates, chocolate bar products, other bar products, fruit gums, hard and soft caramels, chewing gum), alcoholic or non-alcoholic beverages (for example coffee, tea, wine, beverages containing wine, beer, beverages containing beer, liqueurs, spirits, brandies, fruit-containing carbonated beverages, isotonic beverages, soft drinks, nectars, fruit and vegetable juices, fruit or vegetable juice preparations), instant beverages (for example instant cocoa beverages, instant tea beverages, instant coffee beverages), meat products (for example ham, fresh or cured sausage preparations, spiced or marinated fresh or cured meat products), eggs or egg products (dried egg, egg white, egg yolk), cereal products (for example breakfast cereals, muesli bars, precooked ready rice products), dairy products (for example milk beverages, milk ice cream, yogurt, kefir, curd cheese, soft cheese, hard cheese, dried milk powder, whey, butter, buttermilk, products containing partially or entirely hydrolyzed milk protein), products made from soya protein or other soya bean fractions (for example soya milk and products produced therefrom, preparations containing soya lecithin, fermented products such as tofu or tempeh or products produced therefrom, soya sauces), fruit preparations (for example jams, fruit ice cream, fruit sauces, fruit fillings), vegetable preparations (for example ketchup, sauces, dried vegetables, deep-frozen vegetables, precooked vegetables, pickled vegetables, preserved vegetables), snack articles (for example baked or fried potato chips or potato dough products, maize- or peanut-based extrudates), fat- or oil-based products or emulsions thereof (for example mayonnaise, remoulade, dressings), other ready-to-serve meals and soups (for example dried soups, instant soups, precooked soups), spices, seasoning mixtures and in particular powdered seasonings, which are for example used in snack food applications. After incorporation of the aldehydes of type (I) and/or (II) or the corresponding blends according to the invention, these preparations are preparations according to the invention (as an example of articles according to the invention).

Preparations according to the invention may for example assume the form of a semifinished product or a seasoning mixture.

Preparations according to the invention may in particular serve as a semifinished product for the production of further preparations consumed for nutrition or for pleasure, in particular in spray-dried form. Preparations according to the invention may also be nutritional supplements in the form of capsules, tablets (uncoated and coated tablets, for example coatings resistant to gastric juices), sugar-coated tablets, granules, pellets, mixtures of solids, dispersions in liquid phases, as emulsions, as powders, as solutions, as pastes or as other swallowable or chewable preparations.

Preparations according to the invention for oral hygiene purposes are in particular oral and/or dental care products such as toothpastes, tooth gels, tooth powders, mouthwashes, chewing gum and other oral care products.

Further conventional active ingredients, basic materials, auxiliary substances and additives for preparations according to the invention consumed for nutrition or for pleasure or used for oral care may be present in quantities of 5 to 99.999999 wt. %, preferably of 10 to 80 wt. %, relative to the total weight of the preparation. The preparations may furthermore comprise water in a quantity of up to 99.999999 wt. %, preferably of 5 to 80 wt. %, relative to the total weight of the preparation.

Preparations according to the invention (as examples of articles according to the invention) containing aldehydes of type (I) and/or (II) are produced according to a preferred development produced by incorporating one or more aldehydes of type (I) and/or (II) as the undiluted substance, as a solution (for example in ethanol, water or 1,2-propylene glycol) or in the form of a mixture with a solid or liquid carrier (for example maltodextrin, starch, silica gel), other aromas or aroma substances and optionally further auxiliaries and/or stabilizers (for example natural or artificial polysaccharides and/or vegetable gums such as modified starches or gum arabic) into a base preparation consumed for nutrition or for pleasure or used for oral care. Advantageously, preparations assuming solution and/or suspension or emulsion form may also be converted by spray drying into a solid preparation according to the invention (semifinished product).

The spray-dried solid preparations according to the invention (as an example of articles according to the invention) are particularly well suited as a semifinished product for the production of further preparations according to the invention. The spray-dried solid preparations according to the invention preferably contain 50 to 95 wt. % carriers, in particular maltodextrin and/or starch, 5 to 40% auxiliary substances, preferably natural or artificial polysaccharides and/or vegetable gums such as modified starches or gum arabic.

According to a further preferred embodiment, preparations according to the invention are produced by initially incorporating one or more aldehydes of type (I) and/or (II) and optionally other constituents of the preparation according to the invention into emulsions, into liposomes, for example starting from phosphatidyl choline, into microspheres, into nanospheres or also into capsules, granules or extrudates made from a matrix suitable for foodstuffs and products consumed for pleasure, for example from starch, starch derivatives (for example modified starch), cellulose or cellulose derivatives (for example hydroxypropylcellulose), other polysaccharides (for example dextrin, alginate, curdlan, carageenan, chitin, chitosan, pullulan), natural fats, natural waxes (for example beeswax, carnauba wax), from proteins, for example gelatin, or other natural products (for example shellac). In said embodiment, depending on the matrix, the products may be obtained by spray drying, spray granulation, melt granulation, coacervation, coagulation, extrusion, melt extrusion, emulsion methods, coating or other suitable encapsulation methods and optionally a suitable combination of the above-stated methods. In a further preferred production method for a preparation according to the invention, one or more aldehydes of type (I) and/or (II) are initially complexed with one or more complexing agents, for example with cyclodextrins or cyclodextrin derivatives, preferably α- or β-cyclodextrin, and used in this complexed form.

A particularly preferred preparation according to the invention is one in which the matrix is selected such that one or more aldehydes of type (I) and/or (II) is/are released in delayed manner from the matrix, such that a long-lasting action is achieved. A fat, wax, polysaccharide or protein matrix is particularly preferred in this respect.

Further constituents for preparations consumed for nutrition or for pleasure according to the invention which may be used are conventional basic materials, auxiliary substances and additives for foodstuffs or products consumed for pleasure, for example water, mixtures of fresh or processed, plant or animal basic or raw materials (for example raw, roasted, dried, fermented, smoked and/or boiled meat, bone, cartilage, fish, vegetables, fruit, herbs, nuts, vegetable or fruit juices or pastes or mixtures thereof), digestible or non-digestible carbohydrates (for example sucrose, maltose, fructose, glucose, dextrins, amylose, amylopectin, inulin, xylans, cellulose, tagatose), sugar alcohols (for example sorbitol, erythritol), natural or hardened fats (for example tallow, lard, palm fat, coconut oil, hardened vegetable fat), oils (for example sunflower oil, peanut oil, maize germ oil, olive oil, fish oil, soya oil, sesame oil), fatty acids or the salts thereof (for example potassium stearate), proteinogenic or non-proteinogenic amino acids and related compounds (for example γ-aminobutyric acid, taurine), peptides (for example glutathione), native or processed proteins (for example gelatin), enzymes (for example peptidases), nucleic acids, nucleotides, flavor-correcting agents for unpleasant flavor impressions, further flavor-modulators for further generally not unpleasant flavor impressions, other flavor-modulating substances (for example inositol phosphate, nucleotides such as guanosine monophosphate, adenosine monophosphate or other substances such as sodium glutamate or 2-phenoxypropionic acid), emulsifiers (for example lecithins, diacylglycerols, gum arabic), stabilizers (for example carrageenan, alginate), preservatives (for example benzoic acid, sorbic acid), antioxidants (for example tocopherol, ascorbic acid), chelating agents (for example citric acid), organic or inorganic acidulants (for example malic acid, acetic acid, citric acid, tartaric acid, phosphoric acid), bitter substances (for example quinine, caffeine, limonene, amarogentin, humolone, lupolone, catechins, tannins), mineral salts (for example sodium chloride, potassium chloride, magnesium chloride, sodium phosphates), substances preventing enzymatic browning (for example sulfite, ascorbic acid), essential oils, plant extracts, natural or synthetic dyes or coloring pigments (for example carotenoids, flavonoids, anthocyans, chlorophyll and the derivatives thereof), spices, trigeminally active substances or plant extracts containing such trigeminally active substances, synthetic, natural or nature-identical aroma substances or odoriferous substances and flavor-correcting agents.

Dental care products (as the basis for preparations for oral care purposes) which contain one or more aldehydes of type (I) and/or (II) generally comprise an abrasive system (abrasive or polishing agent), such as for example silicas, calcium carbonates, calcium phosphates, aluminum oxides and/or hydroxyapatites, surface-active substances such as for example sodium lauryl sulfate, sodium lauryl sarcosinate and/or cocamidopropyl betaine, humectants such as for example glycerol and/or sorbitol, thickeners, such as for example carboxymethylcellulose, polyethylene glycols, carrageenan and/or Laponite®, sweeteners, such as for example saccharin, flavor-correcting agents for unpleasant flavor impressions, flavor-correcting agents for further, generally not unpleasant flavor impressions, flavor-modulating substances (for example inositol phosphate, nucleotides such as guanosine monophosphate, adenosine monophosphate or other substances such as sodium glutamate or 2-phenoxypropionic acid), cooling active ingredients such as for example menthol, menthol derivatives (for example L-menthol, L-menthyl lactate, L-menthyl alkylcarbonates, menthone ketals, menthane carboxamides), 2,2,2-trialkylacetarrides (for example 2,2-diisopropyl propionic acid methylamide), icilin and icilin derivatives, stabilizers and active ingredients, such as for example sodium fluoride, sodium monofluorophosphate, tin difluoride, quaternary ammonium fluorides, zinc citrate, zinc sulfate, tin pyrophosphate, tin dichloride, blends of different pyrophosphates, triclosan, cetylpyridinium chloride, aluminum lactate, potassium citrate, potassium nitrate, potassium chloride, strontium chloride, hydrogen peroxide, aromas and/or sodium bicarbonate or flavor-correcting agents.

Chewing gums (as a further example of the preparations for oral care purposes) which contain one or more aldehydes of type (I) and/or (II) generally comprise a chewing gum base, i.e. a chewable mass which becomes plastic on chewing, sugars of various kinds, sugar substitutes, other sweet-tasting substances, sugar alcohols, flavor-correcting agents for unpleasant flavor impressions, other flavor modulators for further, generally not unpleasant flavor impressions, flavor-modulating substances (for example inositol phosphate, nucleotides such as guanosine monophosphate, adenosine monophosphate or other substances such as sodium glutamate or 2-phenoxypropionic acid), humectants, thickeners, emulsifiers, aromas and stabilizers or flavor-correcting agents.

In addition to the compound according to the invention, the preparations according to the invention may also contain an aroma composition in order to round off and refine the flavor and/or odor of the preparation. Suitable (additional) aroma compositions contain for example synthetic, natural or nature-identical aroma, odoriferous and flavor substances and suitable auxiliary substances and carriers.

The invention is illustrated in greater detail below with reference to Examples. Unless otherwise stated, all stated values relate to weight.

EXAMPLE 1

Production of a Blend of Aldehydes of Type (I) and (II) (On the Basis of the Method According to DE 39 42 954)

420 g of C12 (70%) and C14 (30%) olefin blend, 3.2 g of triphenylphosphine and 2.2 g of a toluene solution of rhodium 2-ethylhexanoate (corresponding to 125 mg of rhodium), corresponding to a rhodium:phosphorus ratio of 1:100, were introduced into a 1 I stirred autoclave. The temperature was then raised to 130° C. within one hour and hydroformylation was carried out for 6 to 7 hours at this temperature and a pressure of 26 MPa. After cooling to room temperature, the autoclave was flushed with nitrogen. The crude product was filtered (crude yield 442 g) and vacuum-fractionated using a 30 cm Vigreux column.

Yield: 443.5 g (92% of theoretical) Boiling point: 130°-140° C./8 mbar

GC evaluation (20 m ZB-WAX, internal diameter 0.18 μm/60-9-220° C. programmed-temperature vaporization system)

| C13/C15 aldehyde | | |
|---|---|---|
| Branching (number of C atoms in residue R') | C13 area % | C15 area % |
| n (0) | 35.8 | 11.5 |
| Methyl (1) | 24.5 | 10.3 |
| Ethyl (2) | 5.0 | 2.2 |
| Propyl (3) | 2.5 | 1.6 |
| Butyl (4) | 1.6 | 0.9 |
| Pentyl (5) | 1.2 | 0.8 |
| Total | 70.6 | 27.3 |

EXAMPLE 2

Production of a Blend of Aldehydes of Type (I) and (II) (On the Basis of the Method According to DE 43 44 064)

1. 420 g of C12/C14 olefin blend (olefins of the formula A and/or B) were introduced into a 1 I stirred autoclave and heated for 1 hour to 180° C. in the presence of 0.20 g of iron pentacarbonyl.
2. Without separating the isomerization catalyst and after addition of 3.2 g of triphenylphosphine and 2.2 g of a toluene solution of rhodium 2-ethylhexanoate (corresponding 125 mg rhodium, corresponding to a rhodium: phosphorus ratio of 1:100), the resultant olefin isomer mixture was hydroformylated for 6 to 7 hours at a temperature of 130° C. and a pressure of 26 MPa. After cooling to room temperature, the autoclave was flushed with nitrogen. The crude product was filtered (crude yield 440 g) and vacuum-fractionated using a 30 cm Vigreux column.

Yield: 433.2 g (89.9% of theoretical) Boiling point: 130°-140° C./8 mbar

GC evaluation (20m ZB-WAX, internal diameter 0.18 μm/60-9-220° C. programmed-temperature vaporization system)

| C13/C15 aldehyde | | |
|---|---|---|
| Branching (number of C atoms in residue R') | C13 area % | C15 area % |
| n (0) | 5.8 | 2.2 |
| Methyl (1) | 16.4 | 6.4 |
| Ethyl (2) | 11.5 | 4.6 |

-continued

| C13/C15 aldehyde | | |
|---|---|---|
| Branching (number of C atoms in residue R') | C13 area % | C15 area % |
| Propyl (3) | 10.8 | 4.3 |
| Butyl (4) | 21.1 | 8.9 |
| Pentyl (5) | 13.9 | 1.4 |
| Total | 70.5 | 27.8 |

The spectroscopic data of the resultant C13 and C15 aldehydes were determined. The data are shown below.

C13 Aldehydes 1. 2-Butylnonanal
MS: m/z (%)=142 (14, $M^+$−56), 100 (63), 82 (100), 71 (37), 57 (80), 55 (28), 43 (40), 41 (37).

2. 2-Propyldecanal
MS: m/z (%)=156 (7, $M^+$−42), 86 (100), 82 (16), 71 (20), 68 (16), 57 (67), 43 (30), 41 (27).

3. 2-Ethylundecanal
MS: m/z (%)=142 (4, $M^+$−56), 85 (8), 72 (100), 57 (31), 55 (12), 43 (22), 41 (17).

4. 2-Methyldodecanal
MS: m/z (%)=156 (3, $M^+$−42), 140 (9), 71 (18), 58 (100), 57 (24), 55 (16), 43 (23), 41 (19).

5. Tridecanal
MS: m/z (%)=180 (2, $M^+$−18), 154 (16), 124 (16), 110 (20), 96 (53), 82 (89), 68 (54), 57 (100), 43 (75).

C15 Aldehydes 6. 2-Butylundecanal
MS: m/z (%)=182 (19, $M^+$−44), 110 (11), 100 (75), 96 (22), 82 (100), 71 (38), 57 (79), 43 (44).

7. 2-Propyldodecanal
MS: m/z (%)=184 (4, $M^+$−42), 96 (11), 86 (100), 82 (17), 71 (17), 57 (54), 43 (27).

8. 2-Ethyltridecanal
MS: m/z (%)=170 (3, $M^+$−56), 95 (5), 85 (8), 82 (17), 72 (100), 57 (26), 43 (19).

9. 2-Methyltetradecanal
MS: m/z (%)=168 (9, $M^+$−58), 95 (6), 81 (8), 71 (19), 58 (100), 43 (23).

10. Pentadecanal
MS: m/z (%)=208 (4, $M^+$−18), 182 (10), 124 (14), 110 (21), 96 (65), 85 (100), 68 (54), 57 (97), 43 (76).

EXAMPLE 3

Perfume Composition (Odoriferous Substance Composition)

| | |
|---|---|
| Agrumex LC | 10.00 |
| Amarocit ®, 10% in DPG | 10.00 |
| Ambroxide cryst. | 10.00 |
| Basil oil | 10.00 |
| Calone 1951, 10% in DPG | 10.00 |

-continued

| | |
|---|---|
| Cedarwood oil | 10.00 |
| Cedrol cryst. | 50.00 |
| Citral, 10% in DPG | 10.00 |
| Citonellol | 5.00 |
| Coumarin | 10.00 |
| Cyclogalbanat ®, 10% in DPG | 15.00 |
| Dihydromyrcenol | 80.00 |
| Farenal ®, 10% in DPG | 5.00 |
| Galbex, 10% in DPG | 25.00 |
| Globalide ® | 80.00 |
| Globanone ® | 40.00 |
| Hedione | 90.00 |
| Helional | 20.00 |
| Heliotropin | 5.00 |
| Hexenol, cis-3, 10% in DPG | 15.00 |
| Hexenyl salicylate, cis-3 | 10.00 |
| Beta-ionone | 5.00 |
| Iso E Super | 180.00 |
| Isodamascon ®, 10% in DPG | 10.00 |
| Isomuscone (cyclohexadecanone) | 20.00 |
| Isoraldein 70 | 20.00 |
| Ketamber, 10% in TEC | 25.00 |
| Lavandin grosso oil, nat. | 15.00 |
| Lilial | 20.00 |
| Linalool | 20.00 |
| Linalyl acetate | 40.00 |
| Mandarin oil, green, Brazilian | 50.00 |
| Timberol ® | 40.00 |
| Vanillin | 5.00 |
| Veloutone, 10% in DPG | 20.00 |
| Ysamber K ® | 10.00 |
| Total | 1000.00 |

DPG: dipropylene glycol,
TEC = triethyl citrate

Odor description of perfume composition without addition of aldehydes of type (I) and/or (II): fresh, woody.

In the perfumers' opinion, the addition of 3 wt. % of a blend of aldehydes of types (I) and (II) from Example 2 renders this perfume composition fresher, more radiant, better rounded and more harmonious, an aldehyde, coniferous and sweet note appearing and the woody and flowery aspects being enhanced. The aldehydes used impart distinctiveness to the composition due to their intrinsic odor and due to their modifying and enhancing action (booster action) and unite the different odorous elements.

EXAMPLE 4

Perfume Composition (Odoriferous Substance Composition)

| | |
|---|---|
| Allylcyclohexyl propionate | 3.00 |
| Amyl salicylate | 2.00 |
| Benzyl acetate | 64.00 |
| Citronellol | 122.00 |
| Citrate, 10% in DPG | 2.00 |
| Cyclamen aldehyde | 10.00 |
| Dihydromyrcenol | 3.00 |
| Dimethylbenzylcarbinyl acetate | 3.00 |
| Ethyl salicylate, 10% in DPG | 2.00 |
| Eugenol | 3.00 |
| Indoflor, 10% in DPG | 16.00 |
| Galaxolide, 50% in DPG | 164.00 |
| Geraniol | 35.00 |
| Dihydromethyl jasmonate | 6.00 |
| Heliotropin | 4.00 |
| Hexylcinnamaldehyde | 121.00 |
| Vertocitral | 4.00 |

-continued

| | |
|---|---|
| Hydroxycitronellal | 42.00 |
| Indole | 2.00 |
| Isobutyl salicylate | 6.00 |
| Lavandin grosso oil, nat. | 6.00 |
| Acetyl cedrene | 10.00 |
| Lilial | 190.00 |
| Linalool | 35.00 |
| Linalyl acetate | 10.00 |
| Methyl anthranilate, 10% in DPG | 5.00 |
| Nerol | 10.00 |
| Orange oil | 6.00 |
| Phantolide | 4.00 |
| Phenylacetaldehyde dimethylacetal | 6.00 |
| Phenylethyl alcohol | 75.00 |
| Rosatol, 10% in DPG | 6.00 |
| Sandalwood oil | 3.00 |
| Sandranol | 16.00 |
| Trifernal | 2.00 |
| Tonalid | 2.00 |
| Total | 1000.00 |

DPG: dipropylene glycol

Odor description of perfume composition without addition of aldehydes of type (I) and/or (II): flowery, lily of the valley.

In the perfumers' opinion, the addition of 6 wt. % of a blend of aldehydes of types (I) and (II) from Example 1 gives a whole new life to this perfume composition. The impression of floweriness is considerably enhanced. The composition has a more radiant, better rounded and more harmonious effect, an aldehyde, coniferous and sweet note appearing. The aldehydes used impart distinctiveness to the composition due to their intrinsic odor and due to their modifying and enhancing action (booster action) and unite the different odorous elements.

EXAMPLE 5

Shampoo

A blend of aldehydes of type (I) and/or (II) from Example 1 was incorporated at a rate of addition of 0.5 wt. % into a shampoo base of the following composition:

| | |
|---|---|
| Sodium lauryl ether sulfate (for example Texapon NSO from Cognis Germany GmbH) | 12% |
| Cocamidopropyl betaine (for example Dehyton K from Cognis Germany GmbH) | 2% |
| Sodium chloride | 1.4% |
| Citric acid | 1.3% |
| Phenoxyethanol, methyl-, ethyl-, butyl-, and propylparaben | 0.5% |
| Water | 82.8% |

The pH value of the shampoo base was approx. 6. 100 ml of a 20 wt. % aqueous shampoo solution were produced therefrom. Two small strands of hair were washed together in this shampoo solution for 2 minutes and then rinsed for 20 seconds under running, hand-warm water. One strand was wrapped, while wet, in aluminum foil and the second strand was dried with a hairdryer. Both strands were assessed by a panel with regard to odor.

Odor description in each case: clear aldehyde note, strong coniferous note, flowery, sweet, ozone-like.

EXAMPLE 6

Rinse Conditioner

The perfume composition from Example 3 (after addition of 3 wt. % of a blend of aldehydes of types (I) and (II) from Example 2) was incorporated at a rate of addition of 0.5 wt. % into a rinse conditioner base of the following composition:

| | |
|---|---|
| Quaternary ammonium methosulfate (ester quat), approx. 90% (for example Rewoquat WE 18 from Witco Surfactants GmbH) | 5.5% |
| Alkyl dimethylbenzyl ammonium chloride, approx. 50% (for example Preventol R50 from Bayer AG) | 0.2% |
| Colorant solution, approx. 1% | 0.3% |
| Water | 94.0% |

The pH value of the rinse conditioner base was in the range from 2 to 3. Two pieces of fabric were rinsed in a Linetest machine in the rinse conditioning program for 30 minutes at 20° C. with 370 g of a 1% aqueous rinse conditioner solution based on the rinse conditioner base comprising 0.5 wt. % of aldehydes of types (I) and (II). The pieces of fabric were wrung out and then spun for 20 seconds. One piece of fabric was heat-sealed while wet and one was hung up to dry. The two pieces of fabric were then assessed by a panel with regard to odor.

Odor description in each case: flowery, woody, freshly, radiant, aldehyde and coniferous aspects with slight sweet undertones, rounded and harmonious odor impression.

EXAMPLE 7

Washing Powder

The perfume oil composition from Example 4 (after addition of 6 wt. % of a blend of aldehydes of types (I) and (II) from Example 1) was incorporated at a rate of addition of 0.4 wt. % into a washing powder base of the following formulation:

| | |
|---|---|
| Linear Na alkyl benzene sulfonate | 8.8% |
| Ethoxylated fatty alcohol C12-18 (7 EO) | 4.7% |
| Na soap | 3.2% |
| Defoamer DOW CORNING(R) 2-4248S POWDERED ANTIFOAM, Silicone oil on zeolite as carrier material | 3.9% |
| Zeolite 4A | 28.3% |
| Na carbonate | 11.6% |
| Na salt of a copolymer of acrylic and maleic acid (Sokalan CP5) | 2.4% |
| Na silicate | 3.0% |
| Carboxymethylcellulose | 1.2% |
| Dequest 2066 ([[(phosphonomethyl)imino]bis[(ethylenenitrilo)bis (methylene)]tetrakis-phosphonic acid, sodium salt) | 2.8% |
| Optical brightener | 0.2% |
| Na sulfate | 6.5% |
| Protease | 0.4% |
| Sodium perborate tetrahydrate | 22.0% |
| TAED | 1.0% |

Two pieces of fabric were washed in a Linetest machine in the main washing cycle for 45 minutes at 60° C. with 370 g of a 1% aqueous washing powder liquor based on the washing powder base comprising 0.4 wt. % of the perfume oil composition from Example 4 (the pH value of the washing powder liquor is distinctly in the basic range). The pieces of fabric were first rinsed for 5 minutes with cold water, wrung out and then spun for 20 seconds. One piece of fabric was heat-sealed while wet and one was hung up to dry. The two pieces of fabric were then assessed by a panel with regard to odor.

Odor description in each case: strongly flowery, radiant, aldehyde and coniferous note with slight sweet and woody undertones, rounded and harmonious odor impression.

What is claimed is:

1. An odoriferous or aroma substance comprising an aldehyde, substituted in alpha position by an alkyl residue, of the formula

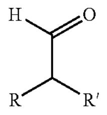

having (I) a total of 13 C atoms, wherein

R means an unbranched alkyl residue having 6, 7, 8 or 9 C atoms and

R' means an unbranched alkyl residue having 2, 3, 4 or 5 C atoms, or (II) a total of 15 C atoms, wherein R means an unbranched alkyl residue having 8, 9, 10 or 11 C atoms and R' means an unbranched alkyl residue having 2, 3, 4 or 5 C atoms, or a blend comprising or consisting of two, three or more such aldehydes of type (I) and/or (II).

2. An odoriferous or aroma substance with coniferous notes comprising an aldehyde, substituted in alpha position by an alkyl residue, of the formula

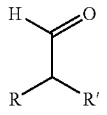

having (I) a total of 13 C atoms, wherein

R means an unbranched alkyl residue having 6, 7, 8 or 9 C atoms and

R' means an unbranched alkyl residue having 2, 3, 4 or 5 C atoms, or (II) a total of 15 C atoms, wherein R means an unbranched alkyl residue having 8, 9, 10, 11 or 12 C atoms and R' means an unbranched alkyl residue having 1, 2, 3, 4 or 5 C atoms, or a blend comprising or consisting of two, three or more such aldehydes of type (I) and/or (II).

3. An odoriferous or aroma substance as in claim 1, to impart, modify and/or enhance an odor and/or flavor note with the following aspects: aldehyde, coniferous, flowery, fatty sweet, ozone-like.

4. A perfumed or aromatized article comprising (a) an aldehyde, substituted in alpha position by an alkyl residue, of the formula

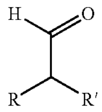

having (I) a total of 13 C atoms, wherein

R means an unbranched alkyl residue having 6, 7, 8 or 9 C atoms and

R' means an unbranched alkyl residue having 2, 3, 4 or 5 C atoms, or (II) a total of 15 C atoms, wherein R means an unbranched alkyl residue having 8, 9, 10, 11 or 12 C atoms and R' means an unbranched alkyl residue having 1, 2, 3, 4 or 5 C atoms, or a blend comprising or consisting of two, three or more such aldehydes of type (I) and/or (II), in a quantity which is sufficient to impart, modify and/or enhance an odor or flavor note of the aldehyde, coniferous, flowery, fatty sweet and/or ozone-like type and (b) one, two, three or more further odoriferous or aroma substances, which in each case do not comprise an aldehyde with 13 or 15 C atoms, wherein the further odoriferous or aroma substance(s) impart(s) a woody and/or flowery odor and/or flavor.

5. The perfumed or aromatized article as in claim 4, further comprising (c) one, two or all the aldehydes selected from the group consisting of pentadecanal, methyl decyl acetaldehyde (2-methyldodecanal) and tridecanal.

6. The perfumed or aromatized article as in claim 4, comprising one, two or more aldehydes of type (I) and one, two or more aldehydes of type (II), wherein the weight ratio of the total quantity of aldehydes of type (I) to aldehydes of type (II) is in the range from 100:1 to 1:10.

7. The perfumed or aromatized article as in claim 4, wherein said article is an odoriferous or aroma substance composition.

8. The perfumed or aromatized article as in claim 7, wherein said odoriferous or aroma substance composition comprises a total quantity of component (a) in the range from 0.00001 to 99.9 wt. % relative to the total quantity of the odoriferous or aroma substance composition.

9. The perfumed or aromatized article as in claim 4, wherein the article is selected from the group consisting of: perfume extracts, eaux de parfum, eaux de toilette, shaving lotions, eaux de cologne, pre-shave products, splash colognes, perfumed tissue wipes, acidic, alkaline and neutral cleaning agents, textile fresheners, ironing aids, liquid detergents, pulverulent detergents, laundry pretreatment agents, laundry rinse conditioners, laundry soaps, laundry tablets, disinfectants, surface disinfectants, air fresheners, aerosol sprays, waxes and polishes, bodycare products, hand creams and lotions, foot creams and lotions, depilatory creams and lotions, after-shave creams and lotions, tanning creams and lotions, hair care products, deodorants and antiperspirants, decorative cosmetic products, candles, lamp oils, incense sticks, insecticides, repellents and fuels.

10. A method for imparting, modifying and/or enhancing an odor or flavor with one, several or all of the notes: aldehyde, coniferous, flowery, fatty sweet and ozone-like, comprising bringing into contact or mixing with a product an organoleptically active quantity of an aldehyde, substituted in alpha position by an alkyl residue, of the formula

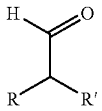

having (I) a total of 13 C atoms, wherein

R means an unbranched alkyl residue having 6, 7, 8 or 9 C atoms and

R' means an unbranched alkyl residue having 2, 3,4 or 5 C atoms, or (II) a total of 15 C atoms, wherein R means an unbranched alkyl residue having 8, 9, 10, 11 or 12 C atoms and R' means an unbranched alkyl residue having 1, 2, 3, 4 or 5 C atoms, or of a blend comprising or consisting of two, three or more such aldehydes of type (I) and/or (II).

* * * * *